(12) United States Patent
Lentz et al.

(10) Patent No.: US 10,279,153 B2
(45) Date of Patent: May 7, 2019

(54) SUPPORTIVE BALLOON CATHETER (71) Applicant: Cook Medical Technologies LLC, Bloomington, IN (US)

(72) Inventors: David Christian Lentz, Bloomington, IN (US); Anders Bro, Malmo (SE); Katrine Birch Rasmussen, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 608 days.

(21) Appl. No.: 14/807,393

(22) Filed: Jul. 23, 2015

(65) Prior Publication Data

US 2016/0022965 A1 Jan. 28, 2016

Related U.S. Application Data

(60) Provisional application No. 62/028,960, filed on Jul. 25, 2014.

(51) Int. Cl.
| | | |
|---|---|---|
| *A61M 29/00* | (2006.01) | |
| *A61M 25/10* | (2013.01) | |
| *A61M 25/00* | (2006.01) | |
| *A61B 17/22* | (2006.01) | |
| *A61M 25/01* | (2006.01) | |
| *A61M 25/09* | (2006.01) | |
| *A61B 17/00* | (2006.01) | |

(52) U.S. Cl.
CPC ........... *A61M 25/104* (2013.01); *A61B 17/22* (2013.01); *A61M 25/005* (2013.01);
(Continued)

(58) Field of Classification Search
CPC .. A61M 25/005; A61M 25/10; A61M 25/104; A61M 25/0026; A61M 25/0032;
(Continued)

(56) References Cited

U.S. PATENT DOCUMENTS

| 4,813,934 A | 3/1989 | Engelson et al. |
| 4,988,356 A | 1/1991 | Crittenden et al. |
| | (Continued) | |

FOREIGN PATENT DOCUMENTS

| EP | 0388486 A1 | 9/1990 |
| EP | 0792656 A1 | 9/1997 |
| | (Continued) | |

OTHER PUBLICATIONS

Extended European Search Report, dated Nov. 26, 2015, pp. 1-7, issued in European Patent Application No. 15177960.0, European Patent Office, Munich, Germany.

(Continued)

*Primary Examiner* — Robert A Lynch
*Assistant Examiner* — Mohamed G Gabr
(74) *Attorney, Agent, or Firm* — Brinks Gilson & Lione (57) ABSTRACT

A supportive balloon catheter which may be used to assist a wire guide in advancing across a lesion which partially or totally occludes an intraluminal passage. The supportive balloon catheter is advanced over the wire guide, close to the location of the lesion. The supportive balloon catheter is then inflated, securing the position of the wire guide in the intraluminal passage. A braid on the catheter may provide additional structural support. The secured catheter restricts the movement of the wire guide advancing across the lesion, preventing kinking or deflection off the surface of the lesion. Once the wire guide has advanced across the lesion, the supportive balloon catheter or a different angioplasty may be used to clear the lesion from the intraluminal passage.

19 Claims, 9 Drawing Sheets

(52) U.S. Cl.
CPC .... *A61M 25/0026* (2013.01); *A61M 25/0052* (2013.01); *A61M 25/0169* (2013.01); *A61M 25/09041* (2013.01); *A61M 25/10* (2013.01); *A61B 2017/00778* (2013.01); *A61B 2017/22001* (2013.01); *A61B 2017/22038* (2013.01); *A61B 2017/22051* (2013.01); *A61B 2017/22054* (2013.01); *A61M 2025/09008* (2013.01); *A61M 2025/1072* (2013.01); *A61M 2210/12* (2013.01)

(58) Field of Classification Search
CPC .......... A61M 25/0043; A61M 25/0045; A61M 25/0052; A61M 25/0169; A61M 25/09041; A61M 25/1029; A61M 2025/0034; A61M 2025/0063; A61M 2025/09008; A61M 2025/1072; A61M 2025/1075; A61M 2025/1093; A61M 2210/12; A61B 2017/00867; A61B 2017/22001; A61B 2017/22051; A61B 2017/22054
See application file for complete search history.

(56) References Cited

U.S. PATENT DOCUMENTS

| | | | |
|---|---|---|---|
| 5,217,434 A | 6/1993 | Arney | |
| 5,906,606 A | 5/1999 | Chee et al. | |
| 6,186,978 B1 * | 2/2001 | Samson | A61M 25/005 604/525 |
| 6,638,243 B2 | 10/2003 | Kupiecki | |
| 6,733,487 B2 | 5/2004 | Keith et al. | |
| 6,976,991 B2 | 12/2005 | Hebert et al. | |
| 7,238,168 B2 | 7/2007 | Sirhan et al. | |
| 7,300,415 B2 | 11/2007 | McMurtry et al. | |
| 7,625,337 B2 | 12/2009 | Campbell et al. | |
| 7,766,049 B2 | 8/2010 | Miller et al. | |
| 8,246,574 B2 | 8/2012 | Jacobs et al. | |
| 8,252,014 B2 | 8/2012 | Fisher | |
| 8,414,524 B2 | 4/2013 | Levine et al. | |
| 2002/0072680 A1 | 6/2002 | Schock et al. | |
| 2002/0198491 A1 * | 12/2002 | Miller | A61M 25/005 604/96.01 |
| 2005/0234427 A1 * | 10/2005 | Eder | A61M 25/0009 604/526 |
| 2011/0060276 A1 * | 3/2011 | Schaeffer | A61M 25/10 604/101.05 |
| 2012/0265134 A1 | 10/2012 | Echarri et al. | |

FOREIGN PATENT DOCUMENTS

| | | |
|---|---|---|
| EP | 2 389 973 A1 | 11/2011 |
| EP | 2491973 A1 | 8/2012 |

OTHER PUBLICATIONS

CODA Balloon Catheter, Martin R. Back, MD, Insert to Endovascular Today, May 2006, 3 pgs.
Guidant™, ZETA vs. BX Velocity (1 pg.).

* cited by examiner

SUPPORTIVE BALLOON CATHETER

CROSS-REFERENCE TO RELATED APPLICATIONS

The present disclosure is related to and claims all benefit pursuant to 35 U.S.C. § 119 of U.S. Provisional Application Ser. No. 62/028,960, filed Jul. 25, 2014, which is incorporated by reference in its entirety.

BACKGROUND

The field of the present invention relates to supportive catheters for use in advancing wire guides across a lesion.

Wire guides are commonly used during angioplasties to pass through narrow passages in the body so that larger catheters and other devices may be advanced through an intraluminal passage along an already established path. Specifically, during an angioplasty, the wire guide is used to cross the portion of the intraluminal passage which is partially or completely occluded by a lesion. However, when the open passage through the lesion is extremely small or completely occluded, it can be difficult for the wire guide to cross the lesion. Furthermore, because wire guides are typically flexible to accommodate curvatures in the vasculature, they often fail to cross the lesion due to the tip of the wire guide being deflected away from the lesion or due to the body of the wire guide kinking in response to longitudinal force being exerted on the wire guide by the operator. To prevent this, support catheters are commonly used to brace the wire guide within the intraluminal passage. The support catheter is advanced over the wire guide as close as possible to the lesion. The wire guide is then advanced in an attempt to cross the lesion. However, although the support catheter prevents kinking of the wire guide, the body of the support catheter frequently bends, flexes, or kinks in response to the force being exerted by the wire guide. This movement of the support catheter makes it more likely that the wire guide will deflect off the lesion or miss a narrow opening which might exist to cross the lesion. It is desirable that a support catheter provide additional support to the wire guide to prevent the tendency of the support catheter, when under stress, to bend, flex, or kink.

The process of attempting to cross a difficult lesion as described above can become time consuming. Because angioplasties are performed under fluoroscopy, it is desirable to conduct the procedure as quickly as possible to minimize the amount of radiation to which the patient is exposed. Additionally, if the wire guide cannot be advanced across the lesion, the angioplasty cannot be performed, and more invasive alternative procedures must be used instead. More invasive procedures pose greater risk of harm to the patient and require longer recovery times.

SUMMARY

A supportive balloon catheter may be used to allow a wire guide to advance across a lesion which partially or completely occludes an intraluminal passage. Once the wire guide has advanced across the lesion, the balloon may then be deflated and re-inflated within the lesion, or different catheters may be advanced over the wire guide to treat the lesion.

In view of this, the supportive balloon catheter system includes a catheter having an inflation lumen and a wire guide lumen. The balloon catheter is advanced over the wire guide to an area close to the lesion, where an inflatable member on the catheter is inflated through the inflation lumen. The inflated balloon catheter presses against the wall of the intraluminal passage, providing support to the wire guide in advancing across the lesion. The catheter may also be braided to provide additional structural support to the wire guide.

The supportive balloon catheter may be used in conjunction with an angioplasty balloon catheter. Once the wire guide has advanced across the lesion, an angioplasty balloon may be advanced over the wire guide and inflated to clear the intraluminal passage. This angioplasty balloon may be advanced from the same side of the lesion as the supportive balloon catheter, or may be advanced from the opposing side of the lesion.

BRIEF DESCRIPTION OF SEVERAL VIEWS OF THE DRAWINGS

The invention may be more fully understood by reading the following description in conjunction with the drawings, in which.

DETAILED DESCRIPTION

Referring now to the drawings, and particularly to FIGS. 1A-1D, a wire guide 101 is shown in an intraluminal passage 100 in the vicinity of a lesion 102. The lesion 102 shown in FIG. 1A may have completely occluded the intraluminal passage 101, or a very narrow channel 110 may be open to the passage of blood. In order for the angioplasty procedure to continue, the wire guide 101 must be advanced at least partially into the lesion 102. However, the narrowness or lack of a channel 110 may prevent the wire guide 101 from being able to easily advance into the lesion 102. If the wire guide 101 is of an insufficient stiffness, it may kink or bend in response to the force exerted on it, instead of advancing through the lesion 102.

Figure 1A:
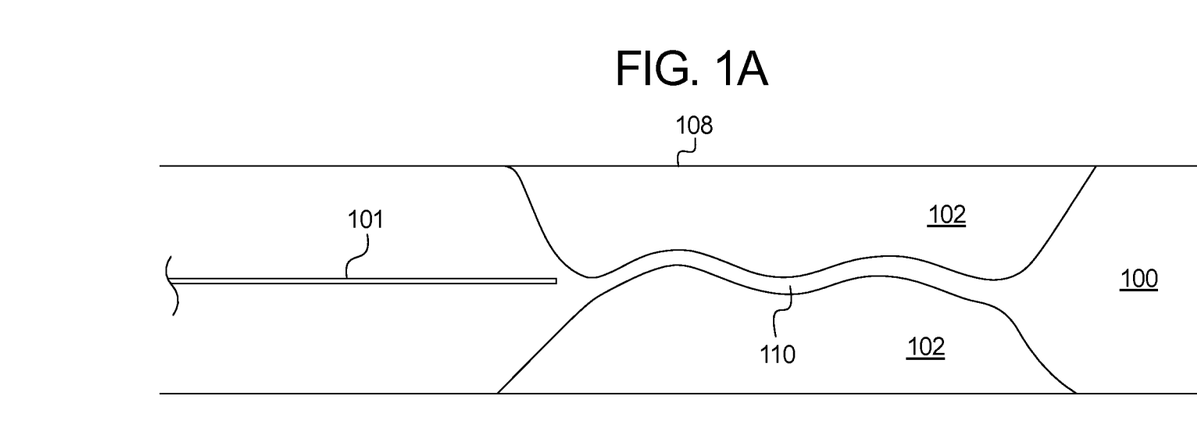
FIGS. 1A-1D are side plan views of a support balloon catheter system within an intraluminal passage, showing a wire guide, and a support balloon catheter in the vicinity of a lesion.
Figure 1B:
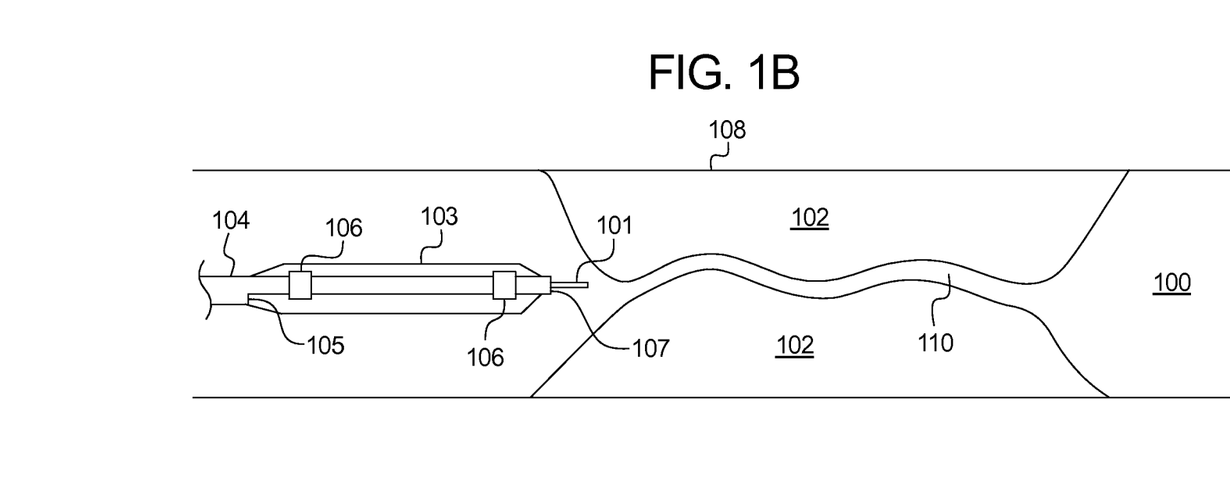

If the wire guide 101 is unable to advance into the lesion 102, a support balloon catheter 104 may be advanced over the wire guide 101 to the lesion 102. As shown in FIG. 1B, it may be advantageous to advance the support balloon catheter 104 as close to the lesion 102 as possible, to give optimal support to the wire guide 101. The wire guide 101 may then be advanced again in an attempt to advance through the lesion 102. During this second attempt, the wire guide lumen 107 of the support balloon catheter 104 may provide support for the wire guide 101, preventing kinking or deflection by constraining the movement of the wire guide 101 within the wire guide lumen 107. It is possible, however, that even with this added support, the support balloon catheter 104 may bend or flex within the intraluminal passage 100, preventing the wire guide 101 from advancing at least partially through the lesion 102.

Figure 1C:
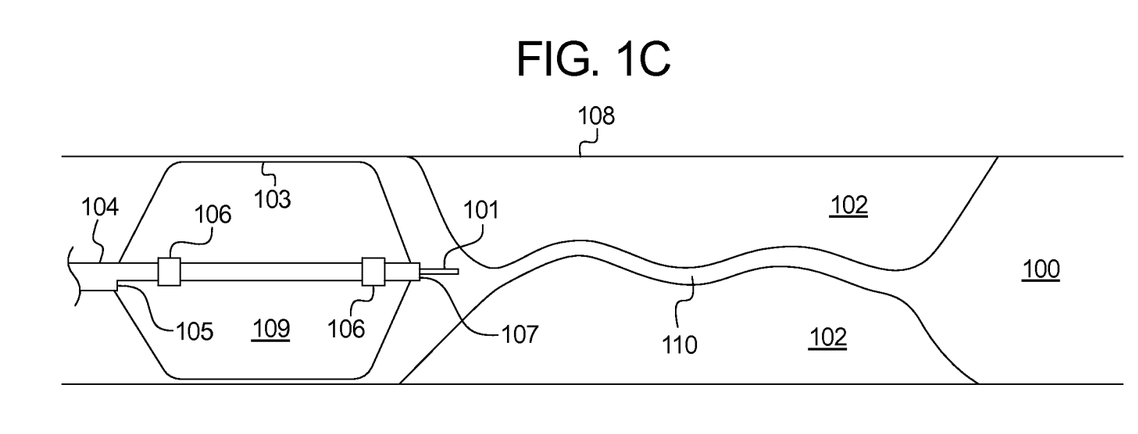

If the uninflated support balloon catheter 104 is unable to support the wire guide 101 to advance through the lesion 102, then the inflatable member 103 of the support balloon catheter 104 may then be inflated to bring the outer surface of the inflatable member 103 into contact with the wall 108 of the intraluminal passage 100, as shown in FIG. 1C. This inflation should occur as near as possible to the lesion 102. It may be desirable to inflate the inflatable member 103 to a sufficient pressure to effectively anchor the position of the support balloon catheter 104 within the intraluminal passage 100. The inflatable member 103 may also be inflated in such a way to expand the wall 108 of the intraluminal passage 100 in the vicinity of, but proximal to the lesion 102, potentially creating or enlarging any channel 110 that might exist through the lesion 102.

Figure 1D:
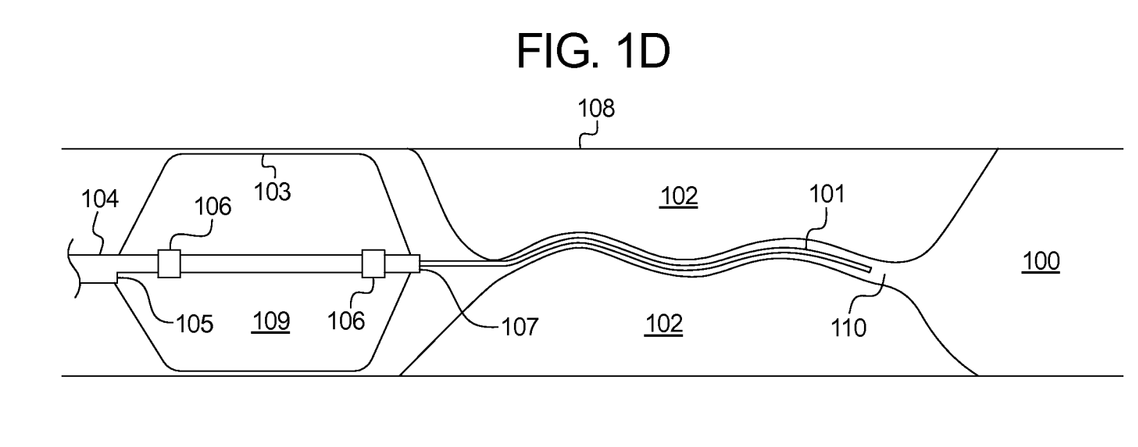

Once the support balloon catheter 104 has been secured by inflation of the inflatable member 103, the movement of the support balloon catheter 104 within the intraluminal passage 100 will be restricted. The wire guide 101 may then be advanced again at least partially through the lesion 102, as shown in FIG. 1D. The wire guide lumen 107 of the support balloon catheter 104 prevents the wire guide 101 from kinking or bending, while the inflation of the inflatable member 103 against the wall 108 of the intraluminal passage 100 prevents the support balloon catheter 104 from bending or flexing.

Once the wire guide 101 has been advanced partially into the lesion 102, the inflatable member 103, if inflated, may be deflated. The support balloon catheter 104 may then be at least partially advanced into the lesion 102. Once the support balloon catheter 104 has advanced, the inflatable member 103 may be inflated to push the lesion 102 against the wall 108 of the intraluminal passage 100, expanding the wall 108 of the intraluminal passage 100 to create a larger channel 110 for blood flow.

Once at least a portion of the lesion 102 has been expanded, the inflatable member 103 may be deflated. If the lesion 102 has been completely expanded, clearing the intraluminal passage 100, the support balloon catheter 104 may be withdrawn over the wire guide 101. If, however, the inflatable member 103 was only able to expand a portion of the lesion 102, then the support balloon catheter 104 may be advanced further through the lesion 102 and reinflated to expand another portion of the lesion 102. The process of inflating, deflating, and advancing may be repeated until the entire lesion 102 has been expanded and the intraluminal passage 100 is clear of any blockages.

The wire guide 101 shown in FIGS. 1A-1D must have a tip with sufficient rigidity to pass through the lesion 102 without deforming. Furthermore, it may be desirable for the wire guide 101 to have a radiopaque tip 306, to allow the operator to observe the movement of the wire guide 101 through the lesion 102 through radioscopy.

The support balloon catheter 104 shown in FIGS. 1A-1D comprises a plurality of lumens, including a wire guide lumen 107 and at least one lumen for inflation fluid 105. The wire guide lumen 107 may end with an opening at the distal end of the balloon catheter 104. The inflation lumen 105 may terminate at several locations along the length of the support balloon catheter, but must have at least an opening to communicate with the interior region 109 of the inflatable member 103.

The inflatable member 103 is arranged on the distal portion of the balloon catheter 104 and may take the form of a balloon, as shown in FIGS. 1A-1D. The inflatable member 103 has an outer surface which defines an interior region 109. The inflatable member 103 may also be pleated with preformed folds to allow for controlled inflation from a tightly wrapped uninflated state. Pleats allow the inflatable member 103 to return to a smaller, uniform shape after deflation, ensuring that the support balloon catheter 104 may be advanced and reinflated.

The length of the inflatable member 103 along the support balloon catheter 104 may differ depending on the intended purpose of the support balloon catheter 104. If the support balloon catheter 104 is intended only to facilitate the advancement of the wire guide 101 across the lesion 102, the inflatable member 103 need only be as long as necessary to adequately secure the support balloon catheter 104 against the wall 108 of the intraluminal passage, which may be relatively short. Alternatively, if the support balloon catheter 104 is intended to both facilitate the advancement of the wire guide 101, and then expand the lesion 102, the length of the inflatable member 103 may be considerably longer, depending on the length of the lesion 102 which is being cleared.

Additionally, the support balloon catheter 104 may have other features such as radiopaque markers 106 on the body of the support balloon catheter 104 to indicate the position of the inflatable member 103 within the intraluminal passage 100. Using the radiopaque markers 106, operators may ensure that the support balloon catheter 104 is deployed as close to the lesion 102 as possible, giving the maximum possible support to the wire guide 101 in attempting to advance through the lesion 102. Additionally, the support balloon catheter 104 and inflatable member 103 may have a hydrophilic coating on the distal portion to increase the pushability and trackability of the support balloon catheter 104 as it advances over the wire guide 101.

FIGS. 2A-2D show an alternative embodiment of the support balloon catheter system. In some situations, a different wire guide 201 and an angioplasty balloon catheter 204 may first be advanced to clear the lesion 102. However, if the lesion 102 mostly or totally occludes the intraluminal passage 100, the different wire guide 201 may be unable to advance through the lesion 102. This may be particularly true since the angioplasty balloon catheter 204 may not be a support balloon catheter with a braid up to the distal end to prevent the different wire guide 201 from flexing or deflecting off the lesion 102. In such a situation, it may be more expedient to advance the wire guide 101 of the support balloon catheter 104 to the opposing side of the lesion 102 and cross the lesion 102 using the support balloon catheter 104 and the method described above and demonstrated in FIGS. 1A-1D.

Figure 2A:
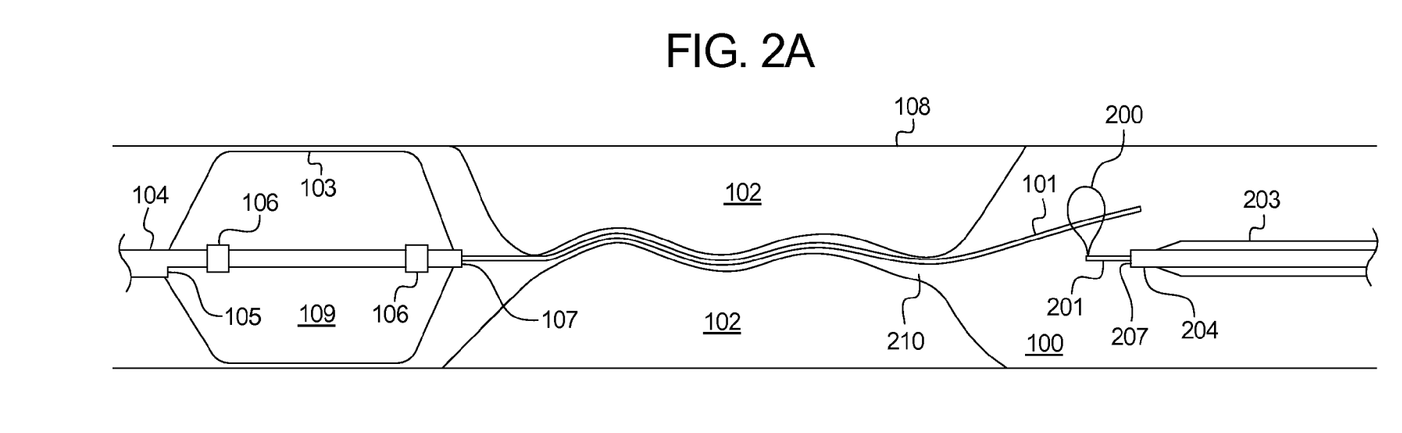
FIGS. 2A-2D are side plan views of a support balloon catheter system within an intraluminal passage, showing a support balloon catheter and an angioplasty balloon catheter arranged on opposing sides of a lesion.
Figure 2B:
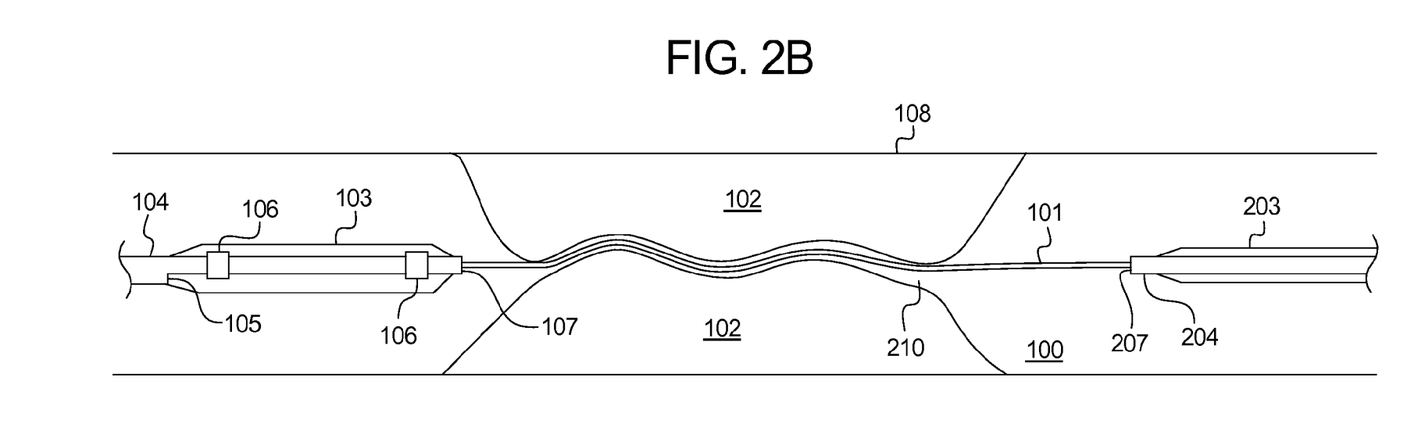

Once the wire guide 101 of the support balloon catheter 104 has crossed the lesion 102, it may be received into a lumen 207 of the angioplasty balloon catheter 204. To facilitate this, the different wire guide 201, if used previously, may need to be retracted. As an alternative, the different wire guide 201 may be substituted with a snare 200 on the distal end of an elongated member. After crossing the lesion 102, the wire guide 101 of the support balloon catheter 104 may be advanced into a loop of the snare 200 as shown in FIG. 2A. The snare 200 then closes around the wire guide 101, and is retracted back into the lumen 207 of the angioplasty balloon catheter 204, as shown in FIG. 2B. Once received inside, the wire guide 101 may be advanced through the lumen 207 of the angioplasty balloon catheter 204. It may be desirable to advance the wire guide 101 to the proximal end of the angioplasty balloon catheter 204 to better control the movement of the angioplasty balloon catheter 204 over the wire guide 101. Concurrently, the original support balloon catheter 104 may be deflated as shown in FIG. 2B and retracted from the body over the wire guide 101.

Figure 2C:
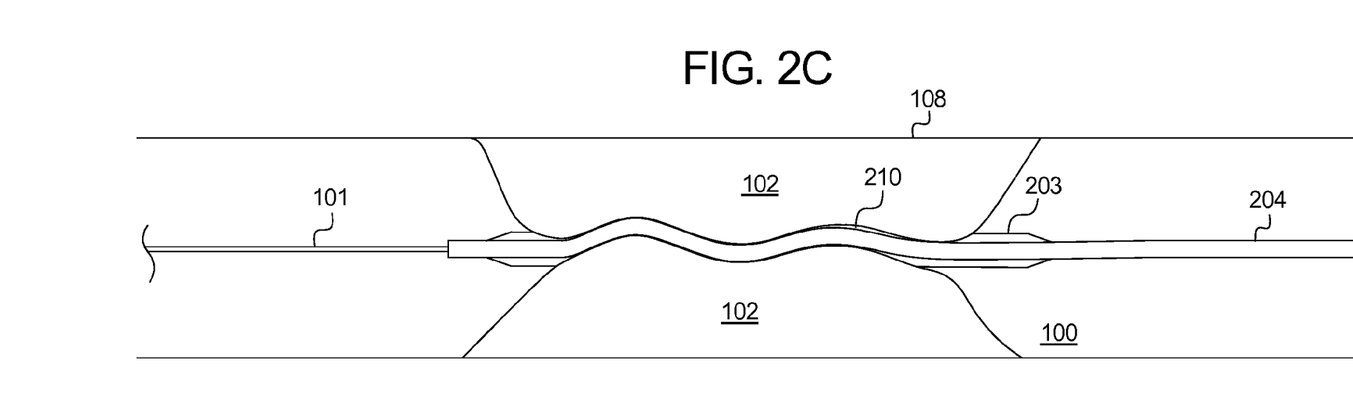
Figure 2D:
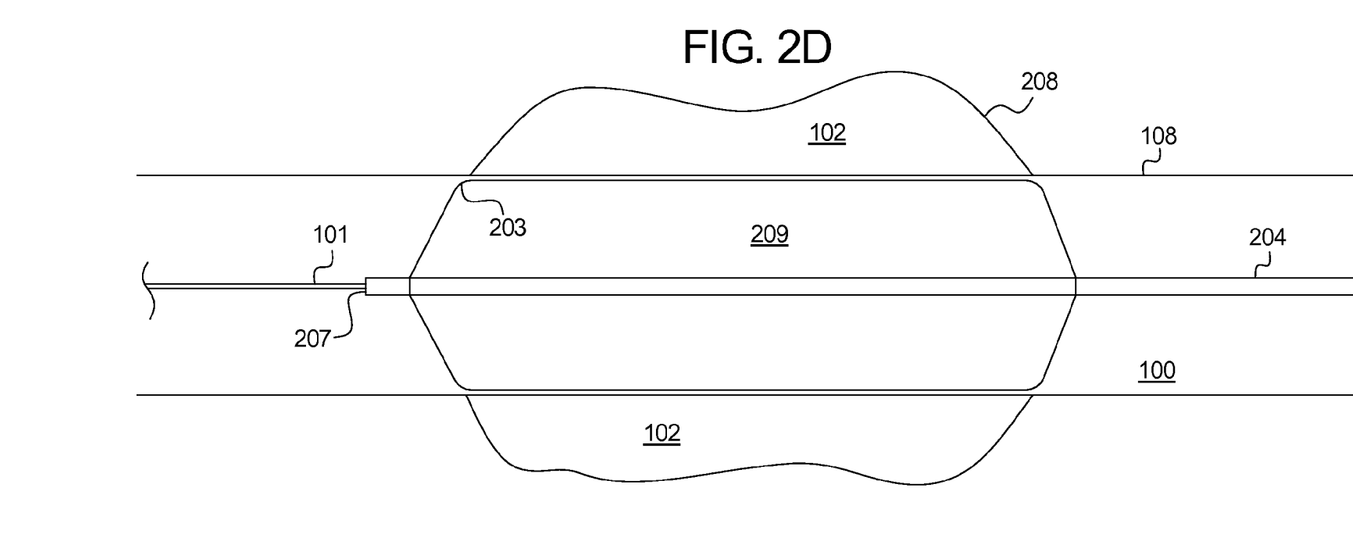

The angioplasty balloon catheter 204 is then advanced over the wire guide 101 at least partially across the lesion 102, as shown in FIG. 2C. Because it lacks a braid, the angioplasty balloon catheter 204 may be more likely to flex and advance easily through the channel 210 crossed by the wire guide 101. Furthermore, the angioplasty balloon catheter may be sized so that the inflatable member 203 is at least as long as the length of the lesion 102. Once the angioplasty balloon catheter 204 has advanced, the inflatable member 203 may be inflated to push the lesion 102 against the wall 108 of the intraluminal passage 100, expanding the wall 108 of the intraluminal passage 100 to create a larger channel 210 for blood flow.

The snare 200 used in the above procedure may comprise at least one loop. It may be desirable that the loop is large enough within the intraluminal passage 100 that little precision is needed to advance the wire guide 101 of the support balloon catheter 104 through the loop of the snare. Additionally, it may be desirable that the loop of the snare 200 be made of a radiopaque material to aid the operator in directing the original wire guide 101 into the loop. Furthermore, it may be necessary to exert the minimum amount of force possible in closing the snare 200 on the wire guide 101. If the snare 200 is closed too tightly, it may kink or divert the distal tip of the wire guide 101, making it more difficult to be received in the lumen 207 of the angioplasty balloon catheter 204.

The angioplasty balloon catheter 204 may comprise a plurality of lumens. The first lumen 207 is used to extend the snare and receive the original wire guide 101, while at least one lumen opens into the interior region 209 of the inflatable member 203 of the angioplasty balloon catheter 204 to inflate the inflatable member 203 using inflation fluid. Additionally, the configuration of the inflatable member 203 on the angioplasty balloon catheter 204 may be different from the inflatable member 103 of the support balloon catheter 104. The inflatable member 103 of the support balloon catheter 104 is primarily configured to press against the wall 108 of the intraluminal passage 100 and may therefore be somewhat shorter in length, but may be capable of being expanded to a diameter at least as large as the intraluminal passage. Comparatively, the inflatable member 203 of the angioplasty balloon catheter 204 should be configured to have a length at least as long as the target lesion 102 which it is being deployed to clear. The result is that the inflatable member 203 of the angioplasty balloon catheter 204 may be substantially longer than the inflatable member 103 of the support balloon catheter 104, but may not need to be inflated to as large a diameter.

Figure 3A:
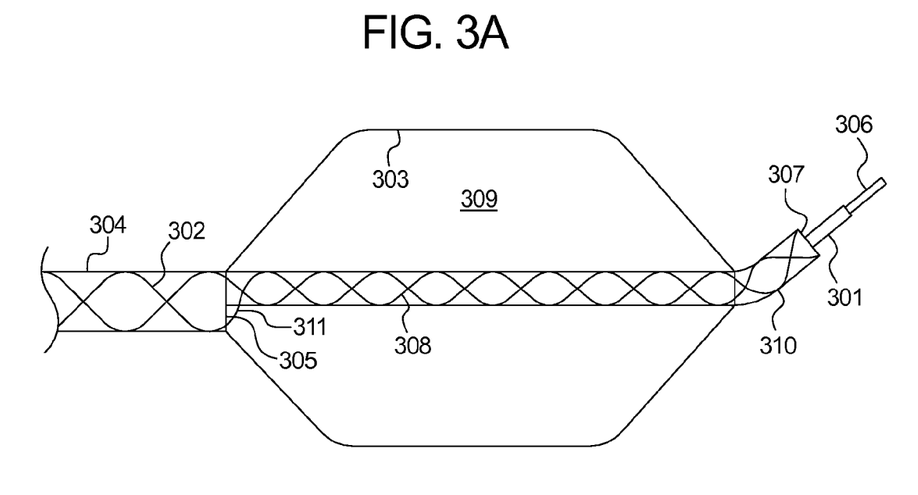
FIG. 3A is a cross-sectional side view of a support balloon catheter system, showing the configuration of the braid of the support balloon catheter.
Figure 3B:
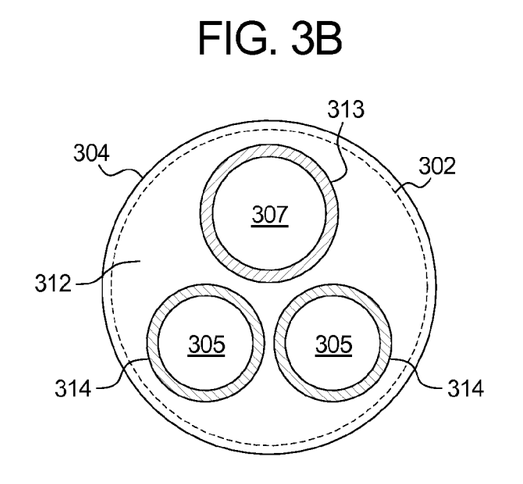
FIG. 3B is a cross-sectional axial view of the support balloon catheter system shown in FIG. 3A.

The support balloon catheter 104 may be configured in a variety of ways. FIGS. 3A and 3B show one possible embodiment of the support balloon catheter 304. FIG. 3A shows a support balloon catheter 304 with two portions having different diameters. The first portion encompasses the wire guide lumen 307, and two inflation lumens 305. The second portion comprises only the wire guide lumen 307. An inflatable member 303 may be attached to the second portion on its distal end, but may be attached to the first portion on its proximal end. The interior region 309 of the inflatable member 303 communicates with the opening of the inflation lumens 305 to allow for inflation.

The support balloon catheter shown in FIGS. 3A and 3B also shows the configuration of a braid 302, 308, 311 which increases the rigidity of the support balloon catheter 304. To provide support to the wire guide 301, it may be desirable for the braid 302, 308, 311 to extend proximally along the body of the support balloon catheter 304 from the proximal side of the inflatable member 303, and distally from the opening of the inflation lumens 305. To accomplish this, the braid 302, 308, 311 will extend along the body of the support balloon catheter 304 through at least a portion of the interior region 309. The braid 302, 308, 311 may extend distally from the interior region 309 of the inflatable member 303 and may extend to as far as the distal end of the body of the support balloon catheter 304. Additionally, the braid 302, 308, 311 may also extend to the proximal end of the body of the support balloon catheter 304.

The support balloon catheter may be comprised of two portions. In the first portion of the support balloon catheter 304, the braid 302 encircles the plurality of lumens 305, 307 of the support balloon catheter 304. In the second portion, the diameter of the braid 308 is reduced, encircling only the remaining wire guide lumen 307. Between these two portions, there may be a transition portion of the braid 311 between the diameters of the first portion and the second portion. For each portion, the braid 302, 308 may be embedded in the material 312 of the support balloon catheter 304. However, the transition portion of the braid 311 may have openings defined by the areas between the filaments of the braid which allow the inflation lumens 305 to communicate with the interior region 309 of the inflatable member 303. Preferably, the braid 308 extends at least to the second portion and may extend to the distal end of the support balloon catheter 304. Additionally, the braid may extend proximally to the proximal end of that support balloon catheter 304.

Various components of the support balloon catheter 304 may be made from a number of different materials. For example, the wire guide lumen 307 and the inflation lumens 305 may be defined by liners 313, 314 made from materials such as polyimide or PTFE. Lumens formed by liners 313, 314 would provide the advantages of isolating the lumens, preventing cross-communication between the inflation lumens 305 and the wire guide lumen 307. The braid 302, 308, 311 may be made of a rigid material such as nitinol and encircles the liners 313, 314. The catheter material 312 is formed around these liners 313, 314 and the braid 302, 308 and may be made from materials such as a thermoplastic polyamide. The inflatable member 303 is applied on the second stage of the support balloon catheter 304 material and may be composed of a material such as polyamide. The interior region 309 may be inflated using a liquid such as saline or contrast fluid.

FIGS. 3A and 3B also disclose other possible features of the support balloon catheter 304. For increased steerability of the wire guide 301, it may be desirable to include a tip 310 on the end of the support balloon catheter 304 which is angularly offset from the longitudinal axis defined by the body of the support balloon catheter 304. The angular tip may be useful in directing the wire guide 301 into a channel 110 through the lesion 102, which is off-center within the intraluminal passage 100. Additionally, it may be desirable to include a radiopaque tip 306 on the wire guide 301 to allow the operator to track the progress of the wire guide 301 through the lesion 102 through radioscopy.

Figure 4A:
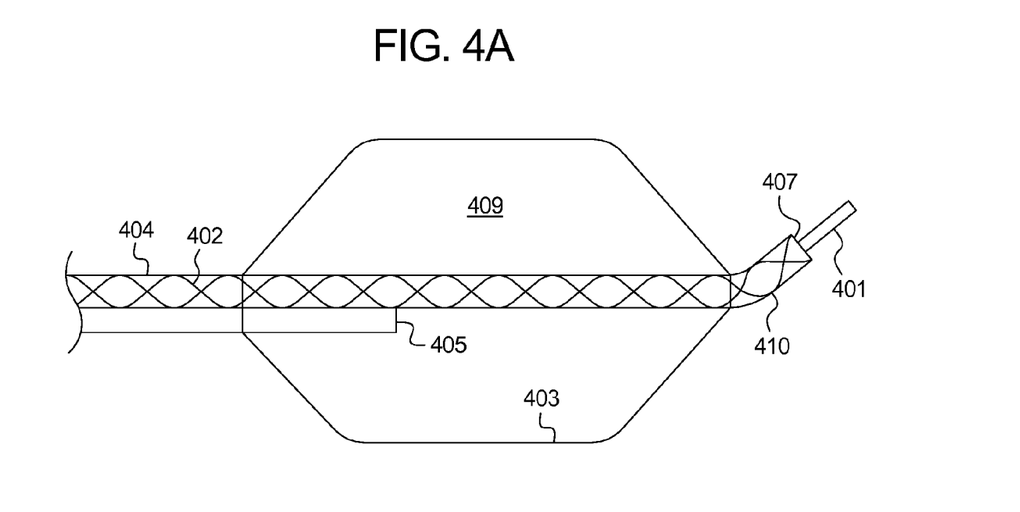
FIG. 4A is a cross-sectional side view of a support balloon catheter system, showing another possible configuration of the braid of the support balloon catheter.
Figure 4B:
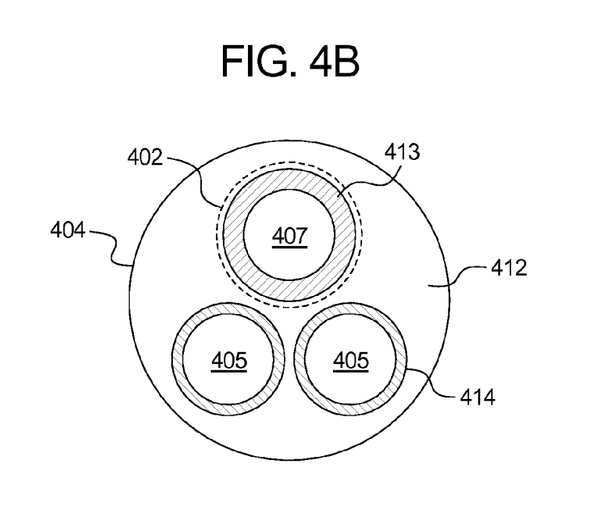
FIG. 4B is a cross-sectional axial view of the support balloon catheter system shown in FIG. 4A.

Another possible embodiment of the support balloon catheter 404 and wire guide 401 may be seen in FIGS. 4A and 4B. The support balloon catheter 404 shown also comprises two inflation lumens 405 and one wire guide lumen 407, each defined by separate liners 413, 414. The two inflation lumens 405 extend and open into the interior region 409 of an inflatable member 403 to allow for communication of inflation fluid. Other features may also be included such as a tip 410 which is angularly offset from the longitudinal axis defined by the body of the support balloon catheter 404.

It may be desirable for the braid 402 to be encased in the catheter material 412, encircling the wire guide lumen 407 for at least a portion of the support balloon catheter's length. A braid 402 encircling the wire guide lumen 407 only would still provide support to the wire guide 401 in attempting to cross the lesion 102, and may also be easier to manufacture than the catheter 304 shown in FIGS. 3A and 3B, as a three staged braid 302, 308, 311 having different diameters would not be needed.

Figure 5A:
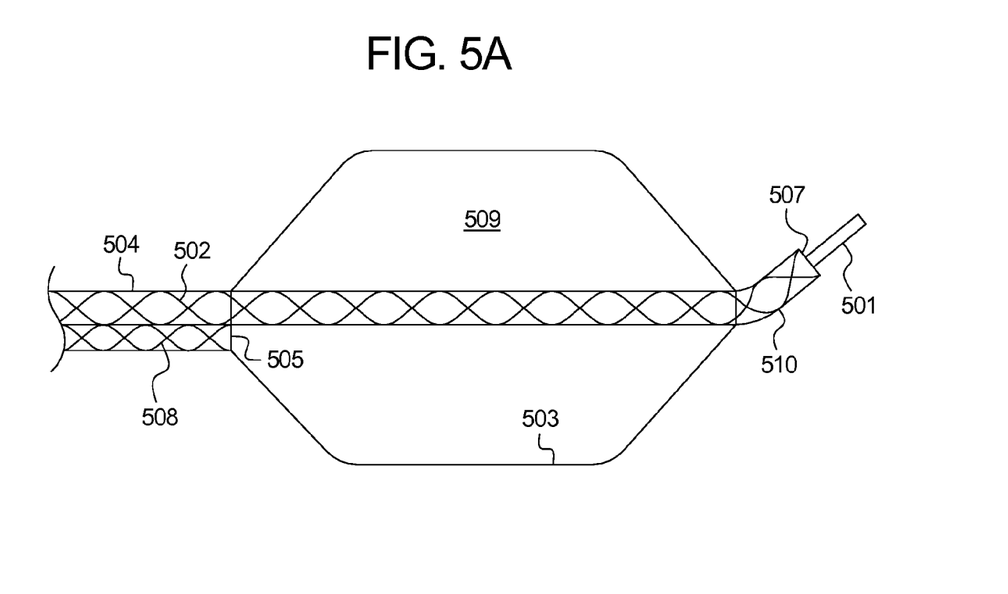
FIG. 5A is a cross-sectional side view of a support balloon catheter system, showing another possible configuration of the braid of the support balloon catheter.
Figure 5B:
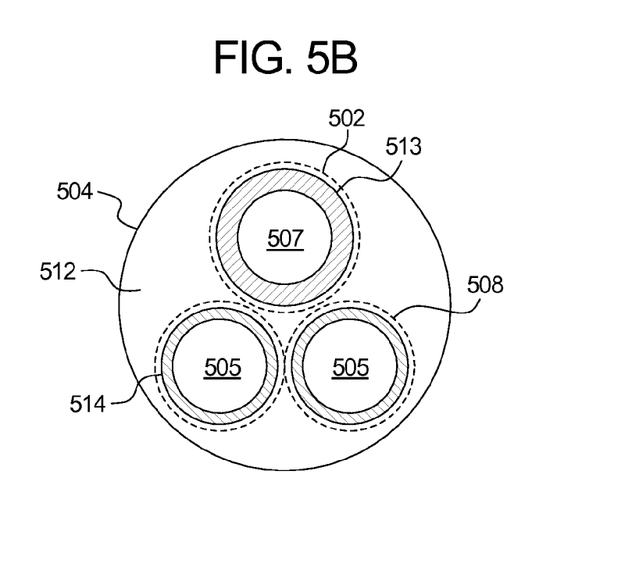
FIG. 5B is a cross-sectional axial view of the support balloon catheter system shown in FIG. 5A.

Another possible embodiment of the support balloon catheter 504 and wire guide 501 may be seen in FIGS. 5A and 5B. The balloon catheter 504 shown also comprises two inflation lumens 505 and one wire guide lumen 507, each defined by separate liners 513, 514. In some circumstances, however, a single lumen for inflation fluid may be sufficient to inflate the inflatable member. The two inflation lumens 505 extend and open into the interior region 509 of an inflatable member 503 to allow for communication of inflation fluid. Other features may also be included such as a tip 510 which is angularly offset from the longitudinal axis defined by the body of the support balloon catheter 504.

It may be desirable for the support balloon catheter 504 to have additional braids. In the embodiment of FIGS. 5A and 5B, three braids 502, 508 are shown so that each of the plurality of lumens 505, 507 is encircled by at least one braid 502, 508 for at least a portion of the support balloon catheter 504. The braids 502, 508 are encased in the catheter material 512. Such a configuration would provide support to the wire guide 501 in attempting to cross the lesion 102 and provide additional support to the support balloon catheter 504 as a whole, and may also be easier to manufacture than the catheter 304, 404 shown in FIGS. 3A and 3B as a three staged braid 302, 308, 311 having different diameters would not be needed.

Figure 6A:
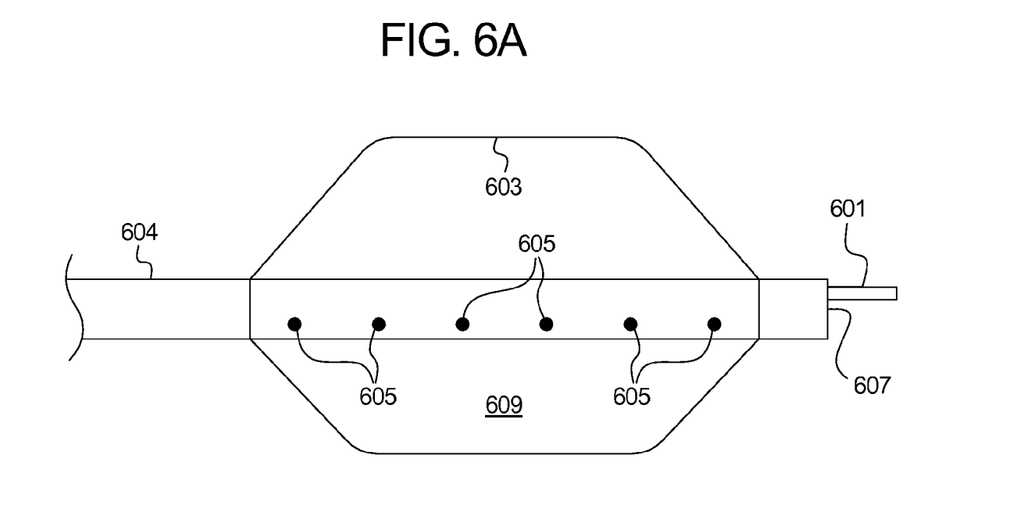
FIG. 6A is a side plan view of a support balloon catheter system showing a support balloon catheter, a wire guide, and side holes along the support balloon catheter's body.
Figure 6B:
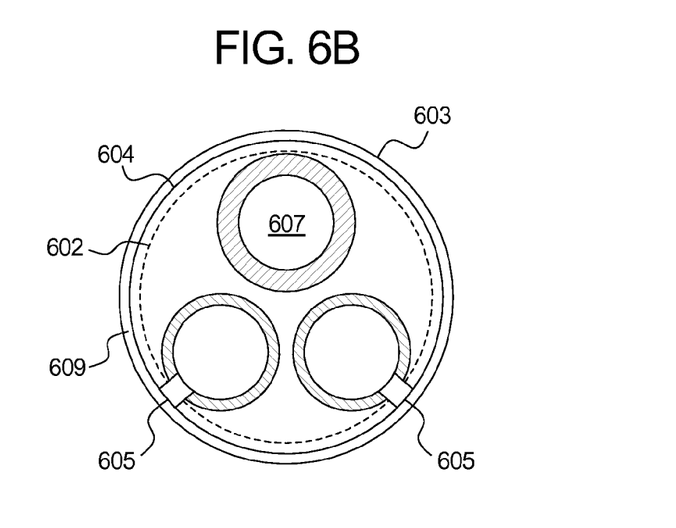
FIG. 6B is a cross-sectional axial view of the support balloon catheter system shown in FIG. 6A.

Another possible embodiment of the support balloon catheter 604 and wire guide 601 is shown in FIGS. 6A and 6B. In the embodiment shown, the catheter comprises of a wire guide lumen 607 and at least one inflation lumen having side openings 605 that communicate with the interior region 609 of the inflatable member 603. For simplicity of construction, it may be desirable to construct the support balloon catheter 604 having a single diameter to the distal end. To facilitate this, it may be necessary to preform side openings 605 in the inflation lumen during the manufacturing of the support balloon catheter 604. The side openings 605 must be large enough and numerous enough to permit efficient communication of inflation fluid to the interior region 609 of the inflatable member 603 depending on what inflation fluid is used. For example, if a low viscosity liquid such as saline is used to inflate the inflatable member 603, more side openings 605 may be preferable to larger diameter side openings 605 to efficiently inflate the inflatable member 603. However, if the a more viscous fluid such as contrast fluid is used to inflate the support balloon catheter 604, larger side openings 605 may be needed to efficiently allow communication of the fluid between the inflation lumen and the interior region 609 of the inflatable member 603. If, as shown in FIG. 6B, the braid 602 encircles the plurality of the lumens, the side openings 605 must be arranged between the gaps in the braid 602 to allow for free communication between the interior region 609 and the inflation lumens.

Figure 7A:
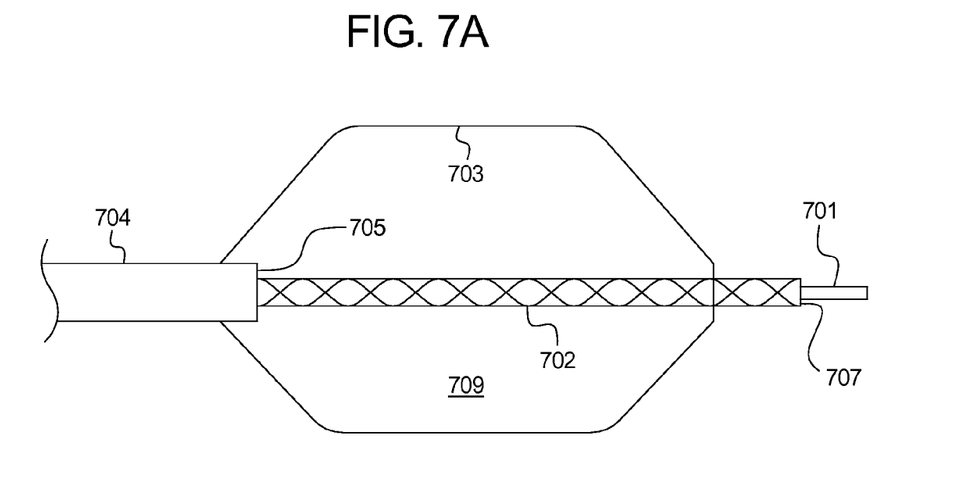
FIG. 7A is cross-sectional side view of a support balloon catheter system, showing an alternative co-axial configuration of the lumens.
Figure 7B:
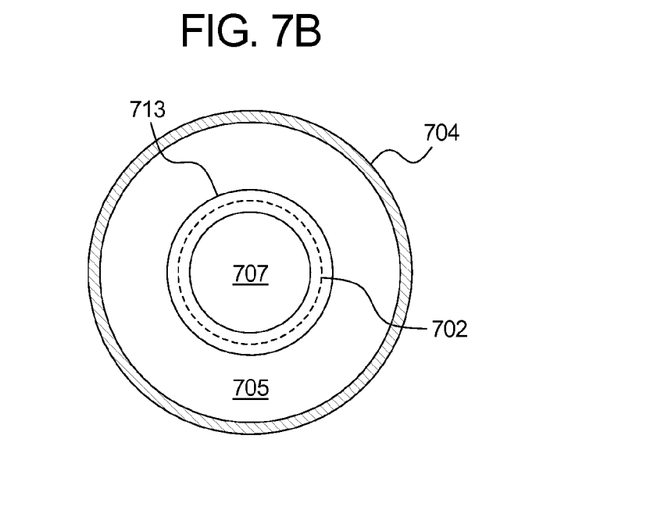
FIG. 7B is a cross-sectional axial view of the support balloon catheter system shown in FIG. 7A.

Another possible embodiment of the support balloon catheter 704 and the wire guide 701 is shown in FIGS. 7A and 7B. In this embodiment, a co-axial arrangement of the lumens 705, 707 is shown, wherein the body of the support balloon catheter has only a single outer inflation lumen 705, and where that lumen 705 encircles an inner wire guide lumen 707. The outer inflation lumen 705 terminates at some point in the interior region 709 of the inflatable member 703 forming an opening through which inflation fluid may be used to inflate the inflatable member 703, while the inner wire guide lumen 707 continues through to the distal end of the support balloon catheter 704.

The co-axial configuration of the lumens 705, 707 is likely simpler and less costly to manufacture, but may provide less stability to the wire guide 701 which is attempting to cross the lesion 102, because the inner wire guide lumen 707 may not be fixed to the outer inflation lumen 605, but instead float freely within. This might be averted by providing at least one support member which connects the body of the outer inflation lumen 705 to the liner 713 of the inner wire guide lumen 707. Alternatively, the wire guide lumen 707 may be stabilized by including a braid 702 embedded in the liner 713 of the wire guide lumen 707. However, it may be preferable to embed the braid 702 in the body of the outer inflation lumen 705 for the first portion of the support balloon catheter 704, and transition the braid 702 to be embedded in the liner 713 of the wire guide lumen 707 distally from the opening of the outer inflation lumen 705, in a manner similar to that shown in FIGS. 3A and 3B.

Accordingly, it is now apparent that there are many advantages of the invention provided herein. In addition to the advantages that have been described, it is also possible that there are still other advantages that are not currently recognized but which may become apparent at a later time.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to embrace them.

We claim:
1. A support balloon catheter, comprising:
a body having a proximal end and a distal end;
a plurality of lumens within the body, including a first lumen for a wire guide, and at least one inflation lumen terminating at an opening, wherein each of the plurality of lumens is spaced apart from each of the other plurality of lumens;

an inflatable member located near the distal end of the body having a proximal side, a distal side, and an outer surface which defines an interior region which communicates with the opening in the at least one inflation lumen; and a braid extending proximally along the body from the proximal side of the inflatable member and distally from the opening of the inflation lumen, wherein the braid comprises a proximal portion and a distal portion, wherein the proximal portion extends proximally from the opening of the inflation lumen and comprises a first diameter such that the proximal portion of the braid encircles the first lumen and the at least one inflation lumen, and the distal portion extends distally from the opening of the inflation lumen and comprises a second diameter which is smaller than the first diameter such that the distal portion of the braid encircles only the first lumen.

2. The support balloon catheter of claim 1, wherein the braid extends distally along the body from the interior region of the inflatable member.

3. The support balloon catheter of claim 1, wherein the braid extends to the proximal end of the body.

4. The support balloon catheter of claim 1, comprising two inflation lumens within the body.

5. The support balloon catheter of claim 1, further comprising additional braids so that each of the plurality of lumens is encircled by at least one braid.

6. The support balloon catheter of claim 1, wherein the plurality of lumens extend to the distal end of the body, and wherein a side opening extending through the body forms the opening of the at least one inflation lumen.

7. The support balloon catheter of claim 1, wherein the distal end of the first lumen is angularly offset from a longitudinal axis defined by the body.

8. The support balloon catheter of claim 1, wherein each of the plurality of lumens is defined by a liner.

9. A method of advancing a wire guide across a lesion, comprising:

advancing a wire guide to a lesion within an intraluminal passage;

advancing a support balloon catheter over the wire guide to the lesion, wherein the support balloon catheter comprises a body having proximal and distal ends, a plurality of lumens including a first lumen for the wire guide and at least one inflation lumen terminating at an opening, a braid extending proximally from the distal end of the body, and an inflatable member located near the distal end of the body having an outer surface which defines an interior region which communicates with the opening in the at least one inflation lumen, wherein at least one the inflation lumen and the first lumen are spaced apart from each other, the braid comprises a proximal portion and a distal portion, the proximal portion extends proximally from the opening of the inflation lumen and comprises a first diameter such that the proximal portion of the braid encircles the first lumen and the at least one inflation lumen, the distal portion extends distally from the opening of the inflation lumen and comprises a second diameter which is less than the first diameter such that the distal portion encircles only the first lumen;

inflating the inflatable member against a wall of the intraluminal passage; thereby restricting movement of the support balloon catheter within the intraluminal passage; and advancing the wire guide at least partially across the lesion.

10. The method of claim 9, further comprising:
deflating the inflatable member after the wire guide has advanced at least partially across the lesion;
advancing the support balloon catheter at least partially across the lesion after deflating the inflatable member; and
inflating the inflatable member after the support balloon catheter has advanced at least partially across the lesion.

11. The method of claim 9, further comprising:
deflating the inflatable member after the wire guide has advanced at least partially across the lesion;
retracting the support balloon catheter from the intraluminal passage over the wire guide;
advancing an angioplasty balloon catheter comprising a second inflatable member through at least a portion of the lesion; and
inflating the second inflatable member after a distal portion of the angioplasty balloon catheter has advanced at least partially across the lesion.

12. The method of claim 11, wherein the angioplasty balloon catheter is advanced from an opposing side of the lesion from where the support balloon catheter was advanced, and wherein the wire guide is received into a lumen of the angioplasty balloon catheter after advancing at least partially across the lesion.

13. The method of claim 12, wherein the wire guide is received into the lumen of the angioplasty balloon catheter by use of a snare.

14. The method of claim 9, wherein the braid extends proximally along the support balloon catheter through the interior region of the inflatable member.

15. The method of claim 9, further comprising additional braids so that each of the plurality of lumens is encircled by at least one braid.

16. The method of claim 9, wherein the plurality of lumens extend to the distal end of the support balloon catheter, and wherein a side opening extending through the support balloon catheter forms the opening of the at least one inflation lumen.

17. A support balloon catheter, comprising:
an elongated member having a proximal portion having a first diameter, a distal portion having a second diameter which is less than the first diameter, a device lumen, and an inflation lumen, wherein the inflation lumen terminates at an opening at the distal end of the proximal portion of the elongated member;
an inflatable member coupled to the elongated member, the inflatable member comprising a proximal end, a distal end, and an outer surface defining an interior region in fluid communication with the opening of the inflation lumen, wherein the elongated member transitions between the proximal portion and the distal portion between the proximal end and the distal end of the inflatable member; and
a braid extending along the elongated member from the proximal end of the inflatable member to the distal end of the inflatable member, wherein the braid encircles the device lumen and inflation lumen within the proximal portion of the elongated member, the braid encircles only the device lumen within the distal portion of the elongated member, and the braid extends distally to a distal end of the elongated member.

18. The support balloon catheter of claim 17, wherein the inflation lumen terminates at the proximal end of the inflatable member.

19. The support balloon catheter of claim 17, wherein the braid extends proximally to a proximal end of the elongated member.

\* \* \* \* \*